US007883697B1

(12) United States Patent
Flambard (10) Patent No.: US 7,883,697 B1
(45) Date of Patent: Feb. 8, 2011

(54) FERMENTED MILK OR VEGETABLE PROTEINS COMPRISING RECEPTOR LIGAND AND USES THEREOF

(75) Inventor: Bénédicte Flambard, Frederiksberg (DK)

(73) Assignee: CHR-Hansen A/S, Horsholm (DK)

( * ) Notice: Subject to any disclaimer, the term of this patent is extended or adjusted under 35 U.S.C. 154(b) by 667 days.

(21) Appl. No.: 11/660,659

(22) PCT Filed: Sep. 5, 2005

(86) PCT No.: PCT/EP2005/054363
§ 371 (c)(1),
(2), (4) Date: Apr. 16, 2007

(87) PCT Pub. No.: WO2006/024673
PCT Pub. Date: Mar. 9, 2006

(30) Foreign Application Priority Data

Sep. 3, 2004 (DK) .............................. 2004 01339

(51) Int. Cl.
*A61K 35/00* (2006.01)
*A61K 35/30* (2006.01)
*A61K 35/55* (2006.01)
*A61K 39/395* (2006.01)
*A61K 45/00* (2006.01)
*A61K 47/00* (2006.01)
*A01N 63/00* (2006.01)

(52) U.S. Cl. ................. 424/93.45; 424/115; 424/143.1; 424/439; 424/563; 424/570; 435/41

(58) Field of Classification Search ....................... None
See application file for complete search history.

(56) References Cited

U.S. PATENT DOCUMENTS

| 5,436,264 | A | * | 7/1995 | Pfister et al. | ................. | 514/415 |
| 5,637,617 | A | * | 6/1997 | Woodward et al. | ........... | 514/567 |
| 6,303,161 | B1 | * | 10/2001 | Takebe et al. | ................. | 426/46 |
| 6,596,301 | B1 | * | 7/2003 | Masuyama et al. | .......... | 424/439 |
| 7,048,906 | B2 | * | 5/2006 | Lin et al. | ..................... | 424/9.2 |
| 2003/0031625 | A1 | * | 2/2003 | Lin et al. | .................... | 424/1.11 |
| 2004/0077624 | A1 | * | 4/2004 | Fox et al. | ............... | 514/210.21 |

FOREIGN PATENT DOCUMENTS

| EP | 0 821 968 A2 | 2/1998 |
| EP | 0 966 969 A1 | 12/1999 |
| EP | 1 016 709 A1 | 7/2000 |
| WO | WO 01/32836 A1 | 5/2001 |
| WO | WO 01/85984 A1 | 11/2001 |
| WO | WO 03/082019 A3 | 10/2003 |
| WO | WO 2004/015125 A1 | 2/2004 |

OTHER PUBLICATIONS

Guthrie (Journal of Family Practice. 1994; 39 (2): 129-133).*
Pool (British Journal of Clinical Practice. 1994; 74: 13-17).*
Anders Fuglsang et al., "Cardiovascular Effects of Fermented Milk Containing Angiotensin-Converting Enzyme Inhibitors Evaluated in Permanently Catheterized, Spontaneously Hypertensive Rats", Applied and Environmental Microbiology, Jul. 2002, pp. 3566-3569.
Yoshiya Hata et al., "A placebo-controlled study of the effect of sour milk on blood pressure in hypertensive subjects", Am J Clin Nutr 1996, 64, 767-771.
Jeffrey A. Pederson et al., "Genetic Characterization of a Cell Envelope-Associated Proteinase from *Lactobacillus helveticus* CNRZ32", Journal of Bacteriology, Aug. 1999, pp. 4592-4597.
Andrew P. Feinberg et al., "A Technique for Radiolabeling DNA Restriction Endonuclease Fragments to High Specific Activity", Analytical Biochemistry, 132, 6-13 (1983).
Stephen F. Altschul et al., "Gapped BLAST and PSI-BLAST: a new generation of protein database search programs", Nucleic Acids Research, 1997, vol. 25, No. 17 3389-3402.
A. Zaza et al., "Heart rate reduction: optimism with some caveats", http://ftp.escardio.org/newscast/stock2001/sipido.htm ; Mar. 8, 2005, pp. 1-2.
Pamela Greengrass et al., "Binding Characteristics of $^3$H-Prazosin to Rat Brain α-Adrenergic Receptors", European Journal of Pharmacology, 55 (1979) 323-326.
Staffan Uhlen et al., "Rat Spinal Cord $\alpha_2$-Adrenoceptors are of the $\alpha_{2A}$-Subtype: Comparison with $\alpha_{2A}$- and $\alpha_{2B}$-Adrenoceptors in Rat Spleen, Cerebral Cortex and Kidney Using $^3$H-RX821002 Ligand Binding", Pharmacology & Toxicology 1991, 69, 341-350.
Jens E Altwein et al., "Introduction: The Changing Therapy of Benign Prostatic Hyperplasia", Scand J Urol Nerphrol 29: 1-6, 1995.
M. Barry et al., "Management of Benign Prostatic Hyperplasia", Annu, Rev. Med. 1997, 48:177-189.
G.S.Brindley, "Pilot experiments on the actions of drugs injected into the human corpus cavernosum penis", Br. J. Pharmac. (1986), 87, 495-500.
Patricia K. Curran et al., "Endogenous $\beta_3$- but Not $\beta_1$-Adrenergic Receptors Are Resistant to Agonist-Mediated Regulation in Human SK-N-MC Neurotumor Cells", Cell Signal, vol. 8 No. 5, pp. 355-364, 1996.
Jean-Christophe Devedjian et al., "Further characterization of human $\alpha_2$-adrenoceptor subtyptes: [$^3$H]RX821002 binding and definition of additional selective drugs", European Journal of Pharmacology, 252 (1994) 43-49.
R. Fuller, "Probiotics in man and animals", Journal of Applied Bacteriology, 1989, 66, 365-378.
Barry Kenny et al., "α1-Adrenoceptor antagonists as treatments for benign prostatic hyperplasia", Exp. Opin. Invest. Drugs (1995) 4(10):915-923.

(Continued)

*Primary Examiner*—Shanon A Foley
(74) *Attorney, Agent, or Firm*—Stephen A. Bent; Foley & Lardner LLP (57) ABSTRACT

The present invention relates to the use of compositions comprising receptor ligands obtainable by a process comprising fermenting a food material, comprising animal milk or vegetable proteins, with lactic acid bacteria to obtain a fermented food or feed material that comprises ligands of specific adrenoreceptors and/or serotonin receptors. The fermented food or feed material is useful e.g. for reducing and/or stabilizing heart rate in a mammal. It may furthermore be used for treatment and/or relief of erectile dysfunctions and for treatment and/or relief of benign prostate hypertrophy (BPH), in a mammal.

12 Claims, 2 Drawing Sheets

OTHER PUBLICATIONS

NM Kim et al., "Alpha-adrenergic receptor blockade by phentolamine increases the efficacy of vasodilators in penile corpus cavernosum", International Journal of Impotence Research (2000) 12, Suppl. 1, S26-S36.

Dominique Langin et al., "[$^3$H]RX821002: a new tool for the identification of $\alpha_{2A}$-adrenoceptors", European Journal of Pharmacology, 167 (1989) 95-104.

Malin C. Levin et al., "The Myocardium-protective Gly-49 Variant of the $\beta_1$-Adrenergic Receptor Exhibits Constitutive Activity and Increased Desensitization and Down-regulation", The Journal of Biological Chemistry, vol. 277, No. 34, Issues of Aug. 23, 2002. pp. 30429-30435.

Anton D. Michel et al., "Identification of a single $\beta_1$ adrenoceptor corresponding to the $\alpha_{1A}$-subtype in rat submaxillary gland", Br. J. Pharmacol. (1989) 98, pp. 883-889.

A. Morales, "Yohimbine in erectile dysfunction: the facts", International Journal of Impotence Research (2000) 12, Suppl. 1, S70-A74.

Stephen J. Peroutka et al., "Multiple Serotonin Receptors: Differential Binding of [$^3$H]5-Hydroxytryptamine, [$^3$H]Lysergic Acid Diethylamide and [$^3$H]Spiroperidol", Molecular Pharmacology, 16, 687-699, 1979.

Ronald F. Borne, "Serotonin: The Neurotransmitter for the '90s", Drug Topics, Oct. 10, 1994, pp. 1-16.

Carol Smith et al., "Beta-Blocker Selectivity at Cloned Human Beta1- and Beta 2- Adrenergic Receptors", Cardiovascular Drugs and Therapy 1999, 13:123-126.

Derwent Abstract 2004-180682,XP-002355394.

* cited by examiner

FERMENTED MILK OR VEGETABLE PROTEINS COMPRISING RECEPTOR LIGAND AND USES THEREOF

FIELD OF INVENTION

The present invention relates to compositions comprising receptor ligands obtainable by a process comprising fermenting a food material, comprising animal milk or vegetable proteins, with at least one lactic acid bacterium to obtain a fermented food material which comprises active components capable of affecting specific adrenoreceptors and/or serotonin receptors and which is useful e.g. for reducing and/or stabilizing heart rate, for treatment and/or relief of erectile dysfunctions and/or for treatment and/or relief of benign prostate hypertrophy (BPH), in a mammal.

TECHNICAL BACKGROUND AND PRIOR ART

Several studies clearly support the notion that a lower resting heart rate is linked to improved survival. In the general population, several studies have shown a strong positive correlation between higher resting heart rate and increased mortality. A two- to three-fold increase in mortality is observed for males with a resting heart rate higher than 88 beats pr. minutes (bpm) compared to a group of males with less than 65 bpm. The heart rate is not only related to cardiovascular mortality but seem also to relate to death from other causes such as cancer. It has even been hypothesized that there is a relation between low heart rate and life expectancy in general (Zaza et al., 2001).

The most common form of cardiovascular disease in the industrialized countries today is coronary artery disease (CAD) or coronary heart disease (CHD) which is the leading cause to heart attacks. CAD and CHD is a "hardening" of the arteries on the surface of the heart, where the term "hardening" refers to a condition that causes the arteries to become so narrowed and stiff that the free flow of blood is blocked.

Lower heart rate is related with better outcome and in particular with a reduced risk of arrhythmias. Higher heart rate may reflect a higher metabolic rate and lower vagal tone thus increasing ischemic risk. Furthermore higher heart rates may also deteriorate ventricular function (Lombardi, F in Zaza et al., 2001). Thus it is not surprising that it has been reported that an important risk factor associated with CAD or CHD is a high heart rate. CAD or CHD is frequently treated with medications. These medications fall into different categories such as:

1. Beta blockers that reduce the workload of the heart by blocking certain chemicals from binding to beta-receptors in the heart.

2. Nitrates that work directly on the blood vessels, causing them to relax and allowing more oxygen-rich blood to reach the heart.

3. Calcium channel blockers that increase blood flow through the heart and may reduce the workload of the heart by blocking calcium ions from signalling the blood vessels to constrict or tighten.

4. Anti platelets (e.g. aspirin) that inhibit the formation of blood clots by decreasing the ability of platelets (microscopic particles found in the blood) to bind together and form a blood clot.

The prevention of a high heart rate in the early stage of the development of the disease can be an alternative to treatment of high heart rate with drugs. A large number of food derived bioactive compounds are currently considered as beneficial for the general well being or as health promoting.

It is known that milk fermented by lactic acid bacteria (LAB) may produce anti-hypertensive effects due to the liberation of peptides from casein in the milk by the proteolytic activity of the lactic acid bacteria. This is for instance described in EP821968 (Calpis Food Industry), EP1016709 (Calpis Food Industry) and WO0132836 (Valio Ltd.).

The article of Yamamoto et al. (1996) discloses that milk fermented with a starter containing *Lactobacillus helveticus* and *Saccharomyces cerevisiae* reduces the systolic and diastolic blood pressure, yet no changes were observed in other indexes, including pulse rate.

WO0185984 (Davisco International Foods, Inc.) also relates to peptides having anti-hypertensive effect (blood reducing effect), where the peptides from an enzymatic digest of whey protein. Changes in heart rate and blood pressure were measured. A significant reduction in mean arterial blood pressure was observed, and except for the observation of the 75 mg/kg dose, which elicited a decrease in heart rate, no significant difference between the heart rate responses occurred at the doses of 30 and 150 mg/kg.

The article of Fuglsang, A., et al. (2002) describes, as the article of Yamamoto et al. (1996), that fermented milk peptides have anti-hypertention properties. However, on page 3569, 1. column, 2. paragraph, it is stated in relation to the tested samples that "the heart rate effect was insignificant versus that of unfermented milk" (i.e. placebo) indicating that the effect on the heart rate was considered insignificant.

The above mentioned article of Yamamoto et al. (1996) and article Fuglsang (2002) and the WO0185984 document indicates that although a lactic acid bacterium fermented product has blood pressure reducing properties there are no reason to believe that it should have heart rate reducing properties as well.

SUMMARY OF THE INVENTION

The problem to be solved by the present invention is to provide an alternative composition useful for reducing heart rate and/or for the relief and/or treatment of benign prostate hypertrophy (BPH) ad/or erectile dysfunction.

The solution is based on that the present inventor surprisingly has identified that by fermenting a food material, preferably milk, with a lactic acid bacterium (LAB), result in that active components that are ligands of several specific adrenoreceptors and also serotonin-receptors and which effect the above mentioned diseases and conditions, are obtained.

Accordingly, a first aspect of the invention relates to the use of a composition obtainable by a process comprising fermenting a food material, which comprises animal milk or vegetable proteins, with at least one lactic acid bacterium to obtain a fermented food material which comprises at least one component that is a ligand of an adrenergic or a serotonin receptor for the manufacture of a product for reducing the heart rate in a mammal.

It follows that another interesting aspect relates to the use as described in the first aspect of the invention for the treatment and/or prevention of benign prostate hypertrophy (BPH) and/or erectile dysfunction.

In a further aspect, the invention provides a fermented food material having heart rate reducing properties and/or which is useful for the prevention and/or treatment of benign prostate hypertrophy (BPH) and/or erectile dysfunction in a mammal and comprising at least one component that is a ligand of an adrenergic or a serotonin receptor produced by the fermentation of the food material with at least one lactic acid bacterium strain. A food material fermented with *Lactobacillus helveticus* strain CHCC5951 (DSM 14998) and/or *Streptococcus thermophilus* is a preferred embodiment.

Food comprising living bacteria is frequently claimed to be particular healthy to ingest (i.e. probiotics). Thus, in a still further aspect the invention provides a fermented food material comprising living bacteria having heart rate reducing properties and/or which is useful for the prevention and/or treatment of benign prostate hyperthrophy (BPH) and/or erectile dysfunction in a mammal is provided. In a presently preferred embodiment the fermented food product comprises living bacterial cells of *Lactobacillus helveticus* strain DSM 14998 and/or *Streptococcus thermophilus* or mutants thereof.

As can be seen from the dose-response experiment (Example 2) it appears possible to obtain even larger response if compositions were made with higher concentrations of the heart rate reducing compound(s). Thus in an interesting aspect the active component(s) isolated from the fermented food material is(are) provided.

In a further aspect, the invention describes the use of the fermented food material or the component that is a ligand of the alpha- or beta-family of adrenoreceptors and/or serotonin receptors isolated therefrom for the manufacture a medicament for the treatment or relief of a coronary artery disease (CAD) or a coronary heart disease (CHD) such as angina pectoris, hypertension, atherosclerosis, stroke, myocardial infarcation, cerebral infarction, and restenosis following angioplasty, arrhythmia, tachyarrythmia, congestive heart failure (CHF), aortic valve regurgitation, chronic renal failure, dyslipidemia, dyslipoproteinemia. and/or for the treatment and/or relief of benign prostate hypertrophy (BPH) and/or erectile dysfunctions.

DEFINITIONS

Prior to a discussion of the detailed embodiments of the invention is provided a definition of specific terms related to the main aspect of the invention.

The term "for reducing the heart rate in a mammalian" denotes reduction of heart rate in relation to the heart rate before administration of the composition as described herein. Before testing on humans, peferably the heart rate reducing properties should be determined in an animal model. In one useful animal model the fermented product is administered to spontaneous hypertensive rats (SHR) by gavage and determine the heart rate for 24 hours after gavage by telemetry in conscious SHR at different time points. Placebo should preferably be the corresponding unfermented food material such as e.g. unfermented milk. For further details see working example 1 herein. But also a model based on normotensive Wistar rats as described in Example 4 can be used to assess the reduction of heart rate.

In the present context the term "ligand" of an receptor is used to describe a component that can bind to the receptor and thereby it may act stimulatory (an agonist) or inhibitory (an "antagonist"). Finally it may compete for the receptor.

"Adrenoreceptors" also known as "adrenergic receptor" are receptors for noradrenaline and adrenalin.

In the present context the term "serotonin receptor(s)" refer to the serotonin receptors that binds [$^3$H]5-hydroxytryptamine as described by Peroutka (1979).

The term "lactic acid bacterium" designates a group of Gram positive, catalase negative, non-motile, microaerophilic or anaerobic bacteria that ferment sugar with the production of acids including lactic acid as the predominantly produced acid, acetic acid, formic acid and propionic acid. Preferably, the lactic acid bacterium is a bacterium of the phylium Firmicutes, more preferably of the class Bacilli, even more preferably of the order Lactobacillales. Within this order a preferred lactic acid bacterium is a bacterium of the family Lactobacillaceae, more preferably of the genus *Lactobacillus*. Preferably it is a *Lactobacillus helveticus* strain. For further details in relation to taxomony reference is made to (Bergey's Manual of Systematic Bacteriology, Second Edition, Volume 1: The Archea and the Deeply Branching and Phototrophic Bacteria). The industrially most useful lactic acid bacteria are found among *Lactococcus* spp., *Streptococcus* spp., *Lactobacillus* spp., *Leuconostoc* spp., *Pediococcus* spp., *Brevibacterium* spp. and *Propionibacterium* spp. Additionally, lactic acid producing bacteria belonging to the group of the strict anaerobic bacteria, bifidobacteria, i.e. *Bifidobacterium* spp. which are frequently used as food starter cultures alone or in combination with lactic acid bacteria, are generally included in the group of lactic acid bacteria.

Embodiment(s) of the present invention is described below, by way of example(s) only.

DETAILED DISCLOSURE OF THE INVENTION

Food material

The food material should comprise animal milk proteins or vegetable proteins.

Preferably it comprises animal milk proteins preferably enumerated by, for example milk protein components, such as whole or defatted animal milk or milk casein. Most preferably the milk is from cows (*Bos taurus*).

Food material with vegetable proteins may preferably be enumerated by, for example corn, corn protein, wheat, wheat protein, soybean, defatted soybean or soybean protein.

Product Comprising at Least One Component that is an Antagonist of an Adrenoreceptor or a Serotonin Receptor which can be Used to Decrease Heart Rate and/or for the Treatment and/or Relief of Benign Prostate Hypertrophy (BPH) and/or Erectile Dysfunction.

As described in example 5 and 6 the use of lactic acid bacteria as described herein provides directly after fermentation a useful amount of the active components that are ligands of specific adrenergic receptors or a serotonin receptor.

Numerous subtypes of adrenergic receptors have been described. They are grouped into three families of receptors—the beta receptors (comprising beta-1 and beta-2), the alpha-1 receptors and the alpha-2 receptors. They are all seven-pass G-protein coupled receptors linked variously to the adenylate cyclase and phosphoinosisitidase second messenger pathway. The catecholamine hormones and neurotransmitters: norepinepherine (noradrenaline) and epinephrine epinephrine (adrenaline) are the normal physiological agonists of the adrenergic receptors and many normal as well as dysfunctional physiological responses related to the regulation of the cardiovascular system are mediated through adrenergic receptors.

The alpha-adreneregic receptors are important mediators of sympathetic nervous system responses, particularly those involved in cardiovascular homeostasis, such as arteriolar smooth muscle constriction and cardiac contraction all of which may lead to increased blood pressure and heart rate. Also the beta-adrenergic receptors plays important role in the regulation of the cardiovascular system. The stimulation of the contractility of the heart e.g. is mediated via activation of the beta-1 adrenergic and beta-2 adrenergic receptors, and increased heart rate is induced via beta-1 adreneregic receptors. Consequently antagonists of these receptors can be useful to decrease or stabilize the heart rate.

Although serotonin receptor antagonists have been ascribed numerous actions in the central nervous system they also appear to be involved in the regulation of the cardiovascular system. The clinically investigated serotonin receptor antagonist, ketaserin, has been found to be an effective anti-hypertensive agent. However, the anti-hypertensive effect may not be ascribed solely to the serotonin receptor antagonizing activity of ketaserin since ketaserin may also block alpha-1 adreno receptors (Borne, 1994).

Thus, one embodiment of the invention is the use of a composition which comprise antagonists against a receptor selected from the group of receptors comprising alpha-adrenergic receptors, beta-adrenergic receptors and serotonin receptors for the manufacture of a product for reducing the heart rate in a mammal.

From example 5 and 6 it is seen that fermentation of cow milk according to the invention produces compounds that are ligands (most likely antagonists) of number of alpha- and beta-adrenoceptors, including the $alpha_1A$-, the $alpha_1B$-, the $alpha_{2A}(h)$-, the $alpha_{2B}(h)$-, the $alpha_{2C}(h)$-, the $beta_1(h)$-, the $beta_2(h)$- and the $beta_3(h)$-adrenergic receptor and even serotonin receptors. Thus an embodiment of the present invention is the use of a composition which comprise antagonists against a receptor selected from the group of receptors comprising the $alpha_1A$-, the $alpha_1B$-, the $alpha_{2A}(h)$-, the $alpha_{2B}(h)$-, the $alpha_{2C}(h)$-, the $beta_1(h)$-, the $beta_2(h)$- and the $beta_3(h)$-adrenergic receptor and serotonin receptors. Most preferred is the use of a composition which comprise antagonists against a receptor selected from the group of receptors comprising the $alpha_{2A}(h)$-, the $apha_{2B}(h)$- and the $beta_2(h)$-adrenergic receptor.

It is well established that sexual health and function are important determinants of quality of life. Disorders such as erectile dysfunction (ED) and female sexual dysfunction are becoming increasingly more important as a result of the aging population. Because this subject is discussed widely in the media, men and women of all ages are seeking guidance in an effort to improve their relationships and experience satisfying sexual lives. Sexual dysfunction is often associated with disorders such as diabetes, hypertension, coronary artery disease, neurologic disorders, and depression. In some patients, sexual dysfunction may be the presenting symptom of such disorders. Additionally, ED is often an adverse effect of many medications. Surprisingly, hormone deficiency is less often the cause of erectile dysfunction than diabetes or vascular disease are. Vascular diseases account for nearly half of all cases of ED in men older than 50 years. Vascular diseases include atherosclerosis, peripheral vascular disease, myocardial infarction, and arterial hypertension. Presently, oral medications used to treat erectile dysfunctions include selective enzyme inhibitors such as sildenafil (sildenafil citrate, Viagra®), vardenafil HCl (Levitra®), tadalafil (Cialis®) and Yohimbine (Yohimbine®, Yocon®).

Alpha-adrenergic receptor blockade by phentolamine and similar compounds increases the efficacy of vasodilators in penile corpus cavernosum (Kim, 2000). Specifically, alpha-2 adreno receptor antagonists have been used for over a century in the treatment of erectile dysfunction using selective drugs such as yohimbine (Morales, 2000). Also Thymoxamine (moxisylyte) that has a competitive and relatively selective blocking action on alpha-1 adreno receptors have shown to produce erection when injected intracavernously (Brindley, 1986). Consequently, both antagonists of the alpha-1 and alpha-2 adreno receptors can be used in the treatment of erectile dysfunction (impotence).

Thus, a further embodiment of the invention is the use of a composition which comprise antagonists against a receptor selected from the group of receptors comprising alpha-adrenergic receptors for the manufacture of a product for treatment or prevention of erectile dysfunction in a mammal.

As cardiovascular diseases account for nearly half of all cases of ED in men older than 50 years. It is conemplated that compositions which in addition to antagonists of the alpha-1 and alpha-2 adreno receptors further comprise beta-adreno receptor antagonists and even serotonin receptor antagonists and further compounds including the gamma butyric acid (GABA) will prove advantageous in the treatment of ED. Consequently an embodiment of the present invention is the use of a composition which comprise antagonists against a receptor selected from the group of receptors comprising alpha-adrenergic, beta-adrenergic and serotonin receptors for the manufacture of a product for treatment or prevention of erectile dysfunction. The product may further comprise agonists of GABA receptors such as GABA itself.

Benign prostatic hyperplasia (BPH) is a common disease in aging males. It is characterized by a change in the size, composition, and function of the prostate gland and leads to obstruction of the bladder and urethra in middle-aged and elderly males. The prostatic smooth muscle tone, mediated primarily through alpha-1 adrenoceptors, appear to be a critical factor in the clinical manifestation of the BPH. As a consequence alpha-1 adrenoceptor antagonists have transformed BPH therapy from surgical to pharmacological intervention (Altwein, 1995; Barry and Roehrborn, 1997). Also alpha-2 adrenoceptor antagonists appear to have beneficial influence on BPH.

As seen in example 6 a number of antagonists to alpha-1 and alpha-2 adrenoceptors, including antagonists to the $alpha_1A$-, $alpha_1B$-, $alpha_{2A}(h)$-, $alpha_{2B}(h)$- and $alpha_{2C}(h)$-adrenoceptor, are produced when fermenting a food material according to the present invention. Thus an important embodiment of the present invention is the use of a composition obtained by fermentation of a food material which comprise antagonists against one or more receptors selected from the group of receptors comprising alpha-adrenergic receptors and beta-adrenergic receptors for the manufacture of a product for treatment or prevention of benign prostate hypertrophy (BPH) in a mammal.

In particular important embodiments of the present invention is the use of a composition obtained by fermentation of a food material which comprise antagonists against one or more receptors selected from the group of receptors comprising the $alpha_1A$-, $alpha_1B$-, $alpha_{2A}(h)$-, $alpha_{2B}(h)$-, $alpha_{2C}(h)$-, $beta_1(h)$-, $beta_2(h)$- and $beta_3(h)$-adrenergic receptors and serotonin receptors. Especially, a product which comprise antagonists against the $alpha_{2A}(h)$-, $alpha_{2B}(h)$- or $beta_2(h)$-adrenergic receptor is preferred.

It is contemplated that a higher efficacy can be obtained if the composition that is obtained by fermentation of a food material comprise more antagonists directed against different relevant receptors e.g. if the fermented food material comprises at least one component that is a ligand of an adrenergic and at least one component that is a ligand of a serotonin receptor, or if the fermented food material comprises at least one component that is a ligand of an adrenergic alpha receptor and at least one component that is a ligand of an adrenergic beta receptor. It is anticipated that the most relevant type of ligands are ligands that have the characteristics of being an antagonist of the receptors in case.

From example 2-5 and in particular example 6 it can be seen that eventhough a dose-dependant relation is established also the unconcentrated fermentate contains antagonists in an amount that result in specific inhibition of specific receptors and which therefore is useful for prevention, relief and/or treatment of BPH and/or erectile dysfunction as well as for reducing heart rate in a mammal. Consequently, it is not necessary to further purify or up-concentrate the ligands from the fermented food material to obtain an effect according to the invention. Thus, in one embodiment, the fermented food material may be packed directly and provided to the market as a food product, preferably a functional food product, or a food product additive, e.g. in a freeze-dried form.

The fermented milk product of the present invention may be any known or future fermented milk product such as e.g. cheese, yoghurt and drinking yoghurt.

It should be understood that the product of the present invention may comprise living microorganisms eliciting a general health beneficial effect. Thus, the product may also be described and marketed as a probiotic product.

In Example 1 this is demonstrated. In short, the results of Example 1 show that fermented milk in itself without any further treatment has good heart rate reducing effect. Further freeze-dried fermented milk could be suspended in neutral milk and thereby give a suitable food product with an effect according to the invention. The freeze-dried fermented milk could therefore be seen as a suitable food additive product.

From Example 5 it appears that active components in the fermented milk product and in the whey fraction binds to the alpha-adrenoreceptor. Accordingly, it is contemplated that the product according to the present invention can be used for the prevention, relief and/or treatment of diseases and conditions where this specific receptor is involved. Such diseases and conditions includes but are not limited to heart diseases, BPH and erectile dysfunctions.

Furthermore, the fact that the active component of the present invention is a ligand antagonist) of the several alpha-adrenoreceptors, beta-adrenoreceptors and even serotonin receptors opens up for combinational administration of the present product with drugs, compounds ligands etc. having a similar effect through another mode of action. In the case of further heart rate reducing compounds such further compounds include the Gamma butyric acid, referred to as GABA. The production of GABA results from the decarboxylation of glutamate (Glu) by the glutamate decarboxylase (GAD; EC 4.1.1.15), in which pyridoxal phosphate acts as the cofactor. It was reported that microorganisms, especially lactic acid bacteria such as *Lactobacillus* sp., *Lactococcus* sp., *Bifidobacterium* sp. and *Streptococcus* sp, have glutamic acid decarboxylase activity and produce GABA from glutamic acid.

GABA has been of interest for many years, due to its health benefits. This molecule constitutes one of the major inhibitory neurotransmitters of the central nervous system. It is found in brain and spinal cord of mammals and indeed very widely distributed in the neurons of the cortex and contributes to motor control, vision, and many other cortical functions. It facilitate blood flow in the brain to increase supply of oxygen so as to accentuate brain metabolism. Further GABA inhibit the secretion of vasopressin (antidiuretic hormone) to decrease the blood pressure by its vascular dilator action and decrease the blood pressure by acting on the vasomotor center of the spinal cord.

GABA Acts Through the Receptors GABA-A and GABA-B Receptors.

Accordingly, it is contemplated that any component that are an agonist of the GABA-A and/or GABA-B receptors (e.g. GABA it self) or any other potential component that are increasing the liberation of GABA in the human body may be included in the product e.g. the fermented milk product of the present invention.

In a preferred embodiment the GABA content of the fermented food or feed product is ensured by including GABA producing microorganisms amongst the microorganisms used to perform the fermentation. In a particular preferred embodiment GABA-producing *Streptococcus thermophilus* are included.

The term "functional food" denotes herein a food product where the consumer in some way is informed that it has a useful function in relation to the diseases and/or conditions mentioned hereinbefore. When the term food is used it may also be feed. However, a food product is preferred.

Accordingly, an embodiment of the invention relates to a use as described herein where the composition is a food product comprising the active components with properties as described obtainable by a process comprising the following steps:
(i) preparing a fermented food material according to a process for preparing the active components with properties as described herein,
(ii) drying the fermented food material, and
(iii) packing it in a suitable way to get a food product or food product additive.

Step (ii) is Preferably Freeze-Drying.

The term "packing" should be understood broadly. It denotes that once a food material is fermented and a fermented food material is obtained, the fermented food material should be packed in order to could be provided to the consumer. It may be packed in a bottle, a tetra-pack, etc. Preferably, on the package or in corresponding marketing material is indicated that the product has heart rate reducing properties. This applies for any aspects or embodiments of a product as described herein.

As shown in example 1 the lactic acid bacteria in the food product may be provided as cells of the bacteria. Heat-treated fermented food material also elicited a heart rate reducing effect, consequently, the contemplated effects are to be expected from using cells of the lactic acid bacteria.

In preferred embodiments the fermented food product contains live bacteria cells that are beneficial to the health of a mammal host. Such microorganisms are frequently referred to as probiotics.

In general probiotics constitute a class of microorganisms defined as live microbial organisms that beneficially affect animal or human hosts. Lactic acid bacteria are in general recognised as being useful as probiotics or probiotically active organisms, especially lactic acid bacteria that are found among *Lactobacillus, Streptococci* and *Bifidobacterium* species (Fuller (1989)).

Use of a Product Having the Properties as Previously Described

As illustrated in example 1 the heart rate reducing properties can be determined by administrating the product to spontaneous hypertensive rats (SHR) by gavage and determine the heart rate for 24 hours after gavage by telemetry in conscious SHR at different time points. However also other animal models are useful for evaluating the heart rate efficacy of the fermented product. One example is the model of normotensive Wistar rats described in example 4.

The product may be used in a treatment of a coronary artery disease (CAD) or a coronary heart disease (CHD) such as angina pectoris, hypertension, atherosclerosis, stroke, myocardial infarcation, cerebral infarction, and restenosis following angioplasty, arrhythmia, tachyarrythmia, congestive heart failure (CHF), aortic valve regurgitation, chronic renal failure, dyslipidemia, dyslipoproteinemia. In such case the product is preferably a medicament. Preferred diseases are angina pectoris, hypertension, and atherosclerosis.

In addition to the conditions just mentioned the issue of fluctuations of the heart rate attracts interest. In Example 1, 2 and 3 it is demonstrated that the fermented product effectively decreases heart rate but surprisingly also decreases fluctuations in the heart rate during the activity period of the experimental animals. In particular in stressed situations where significant heart rate fluctuations are frequently observed the damping of the fluctuations in the heart rate may be an important feature since changes in heart rate correlates with mortality in an experimental model (Zaza et al 2001).

Because coronary artery diseases tend to develop over a long period of time, there are opportunities throughout one's lifetime to prevent or control it. Preventive care can begin early, thus reducing the speed at which atherosclerosis develops. Therefore, another preferred use of the product is in a preventive manner. In such case the product may preferably be a food product or food additive, which people can consume in a daily or continuous manner.

Preferably the product has a heart rate reducing effect that is at least 10% over placebo where placebo is defined above as the corresponding unfermented food material. Using this definition, more preferably the product has a heart rate reducing effect that is at least 15% over placebo, even more preferably the product has a heart rate reducing effect that is at least 20% over placebo and most preferably the product has a heart rate reducing effect that is at least 25% over placebo.

Subsequent Purification of the Component that is a Receptor-Ligand from the Fermented Food Material As stated above, the use of the lactic acid bacteria, as described herein, provides directly after the fermentation a useful amount of the active components with very good heart rate reducing properties as well as contemplated effects on other conditions and diseases as previously mentioned.

However, in some circumstances it may be preferred to perform a subsequent purification or up-concentration of the active components from the fermented food material. This may for instance be when the active components are to be used in a medicament such as a pharmaceutical tablet, or other dosage form which requires a high concentration of the active component. Accordingly, in an embodiment of the invention the product is a medicament.

Furthermore, example 1 shows that the heart rate reducing effect is proportional to the concentration factor of the product.

Accordingly, an embodiment of the invention relates to a use as described herein where the fermented food material is further processed in a way that purify or up-concentrate the active components that is a ligand of the alpha-adrenoreceptors, beta-adrenoreceptors or serotonin receptors obtainable by a process comprising the following steps:

(i) Preparing a fermented food material according to a process for preparing the active components having the properties as described herein, (ii) The fermented food material of step (i) is further processed in a way that purifies or up-concentrate the active components with heart rate reducing properties, (ii) Packing it in a suitable way to get a product.

This corresponds to a situation where one wants a relatively high concentration of the active components with the wanted properties in the product.

If the product is a food product the process may comprise a further step (iv) where the up-concentrated active components of (ii) is added to the food product.

A preferred embodiment for up-concentration according to step (ii) above is where the fermented food material comprising the active components is centrifuged, and the resulting supernatant comprising the active components are recovered. If the food material is milk then such a product could be whey. As can be seen in example 1, whey is a product with excellent heart rate reducing properties. Accordingly in a preferred embodiment the product is whey, however other fractions of the fermentated food or feed material may also be considered.

The centrifugation may preferably be performed, for example, at 2,000 to 20,000 rpm for 1 to 20 minutes. The centrifugation may also be performed in a centrifugator.

The resulting supernatant may be subjected to further purifying treatment with a reverse-phase resin, for obtaining a sample in which the content of the active components is increased. The purifying treatment with a reverse-phase resin may be performed by absorption and elution, by reverse-phase resin, and/or by reverse-phase chromatography, thereby increasing purity of the active components.

For further technical details in relation to this reverse-phase resin protocol reference is made to EP821968.

Alternatively, the fermented food material is further processed in a way wherein a nanofiltration is performed on the fermented food material. This may be done in order to remove lactic acid or monovalent ions from the fermented food material.

For further technical details in relation to this nanofiltration protocol reference is made to WO01/32905.

As described in Example 2, there is a clear dosage dependent effect on the heart rate of the whey products concentrated up to a factor of 21 times. There is no indication in the experiment suggesting that a stationary or asymptotic level was reached, indicating that compositions comprising high amounts of the active compound(s) can have important uses as medicaments.

Fermentation

In the process of the present invention, the food material is fermented by lactic acid bacteria under operating conditions, which may be varied depending on the types of the food material and/or the combination of the lactic acid bacteria. Preferably, if the food material is not already an aqueous solution, food material is dissolved in a suitable aqueous solution, which is then admixed with lactic acid bacteria and cultivated by way of fermentation.

The culturing of the lactic acid bacteria may be performed by adding a pre-cultured lactic acid bacteria starter culture to the food material medium, which may have been previously heat-sterilized and cooled to the predetermined temperature for incubation. The inoculation amount of the lactic acid bacteria starter may preferably be $10^5$ to $10^7$ cells of lactic acid bacteria/ml medium, however—depending on the specific starter culture—other amounts of starter cultures should be considered as well. The temperature for incubation is usually 20 to 50° C. and preferably 30 to 45° C. The incubation time is usually 3 to 48 hours and preferably 6 to 24 hours. Particularly, it is preferred to perform cultivation in the medium having pH in a range of 3.5 to 7, more preferably 5 to 6, in order to perform cultivation of lactic acid bacteria efficiently. Further, it is preferred to perform a so-called "pH-stat" cultivation maintaining pH in a range of 4 to 7. The incubation may be terminated, without restriction, when the number of lactic acid bacteria exceeds $10^8$ cells/ml.

A preferred embodiment relates to a process, as described herein, wherein the fermenting of the food material is performed under conditions, which produce from 0.5 to 25 mg active components per 100 ml of the food material, more preferably which produce from 1 to 5 mg active components per 100 ml of the food material.

Mammal

Mammal include animals such as domesticated animals (e.g. cats and dogs), pigs, cows, lambs. In a preferred embodiment the mammal is a human.

Lactic Acid Bacterium

As stated above, the term "lactic acid bacterium" designates a group of Gram positive, catalase negative, non-motile, microaerophilic or anaerobic bacteria that ferment sugar with the production of acids including lactic acid as the predominantly produced acid, acetic acid, formic acid and propionic acid.

Among others, it includes species of lactic acid bacteria belonging to genus *Lactobacillus*, such as *Lactobacillus helveticus, Lactobacillus delbruekii* subsp. *bulgaricus*, etc., lactic acid bacteria belonging to genus *Lactococcus*, such as *Lactococcus lactis*, lactic acid bacteria belonging to genus *Streptococcus*, such as *Streptococcus salivarius* subsp. *thermophilus*, lactic acid bacteria belonging to genus *Leuconostoc*, such as *Leuconostoc lactis*, lactic acid bacteria belonging to genus *Bifidobacterium*, such as *Bifidobacterium longum* or *Bifidobacterium breve*, and lactic acid bacteria belonging to genus *Pediococcus*.

The lactic acid bacteria may be used as a mixture with other microorganisms, e.g. yeasts. Numerous different lactic acid bacteria are public available to the skilled person and it is contemplated that particular useful mixtures include a combination of *Lactobacillus helveticus* and *Streptococcus thermophilus*. Reference is e.g. made to Deutsche Sammlung von Mikroorganismen and Zellkulturen GmbH (DSMZ); and the Internet taxonomy browser of NCBI [at filing date available at worldwideweb.ncbi.nlm.nih.gov/.].

A sample of a particular preferred *Lactobacillus helveticus* strain CHCC5951 has been deposited at DSMZ (Deutsche Sammlung von Mikroorganismen und Zellkulturen GmbH) under the accession number DSM 14998 with a deposit date of $15^{th}$ May 2002. The deposit has been made under the conditions of the Budapest Treaty on the International Recognition of the Deposit of Microorganisms for the Purposes of Patent Procedure.

Accordingly, a particular preferred embodiment relates to a use as described herein where the lactic acid bacterium is *Lactobacillus helveticus* with the registration number DSM 14998 is used. In a further interesting embodiment and in particular for reducing heart rate, the above mentioned strain DSM 14998 is used in combination with a *Streptococcus thermophilus* strain.

Further, a sample of a *Lactobacillus helveticus* strain CHCC4080 has been deposited at DSMZ (Deutsche Sammlung von Mikroorganismen und Zellkulturen GmbH) under the accession number DSM 14997 with a deposit date of $15^{th}$ May 2002. The deposit has been made under the conditions of the Budapest Treaty on the International Recognition of the Deposit of Micro organisms for the Purposes of Patent Procedure.

EXAMPLES

Example 1

In Vivo Test of Heart Rate Reducing Properties

Materials and Methods

Strains and Cultivation

Strains were streaked on MRS agar and incubated anaerobically for 48 h at 37° C. A single colony was picked, inoculated into MRS broth and grown overnight at 37° C. Stock cultures were prepared from this overnight culture and were stored at −80° C. in 20% glycerol. The strains were precultivated in milk overnight and inoculated 1% (v/v) in fresh milk for the fermentation.

Preparation of the Samples

Whey: Sample 1

The milk (9.5% of protein content) was fermented with the strain of single culture for 16 hours with an inoculation level of 1% (v/v). The fermented product was centrifuged, the pellet was discarded and the whey was filtered through a 0.45 mm filter and freeze-dried. A second fermentation, fermented under the same conditions as the first one, was centrifuged and the whey fraction obtained. The pellet was discarded and the whey was filtered through a 0.45 mm filter and frozen. The whey was used to solubilize the freeze-dried whey powder to concentrate it with a factor 21 before feeding the rats.

Freeze-Dried Fermented Milk Dissolved in Whey: Sample 2

The milk (9.5% of protein content) was fermented with the strain of single culture for 16 hours with an inoculation level of 1% (v/v). The total product was freeze-dried. A second fermentation, with the same conditions as the first one, was centrifuged. The pellet was discarded and the whey was filtered through a 0.45 mm filter and frozen. The whey was used to solubilize the freeze-dried fermented milk powder to concentrate it with a factor 5 before feeding the rats.

Freeze-Dried Fermented Milk Dissolved in Milk: Sample 3

The milk (9.5% of protein content) was fermented with the strain of single culture for 16 hours with an inoculation level of 1% (v/v). The total product was freeze-dried. Milk (9.5% of protein content) was used to solubilize the freeze-dried powder to concentrate it with a factor 5 before feeding the rats.

Overnight Milk Fermentation Product: Sample 4

The milk (9.5% of protein content) was fermented with the strain of single culture for 16 hours with an inoculation level of 1% (v/v).

Overnight Milk Fermentation Product Heat-Treated: Sample 5

The milk (9.5% of protein content) was fermented with the strain of single culture for 16 hours with an inoculation level of 1% (v/v).

Spontaneously Hypertensive Rats

Spontaneously Hypertensive Rats (SHR) was obtained from IFFA CREDO (a Charles River company), Lyon, France.

Each treatment was administered between 9:15$^h$ and 9:30$^h$ by gavage and each animal received a total volume of 2.5 ml per animal.

Experimental Design

Three Groups were Formed:

Group 1 (n=16): receiving treatment 1 (milk; n=16)

Group 2 (n=12): receiving successive treatments, each administration separated by a 3-day washout period Groups: 1) Placebo (Milk)
2) Sample 1 (Freeze-dried whey suspended in whey. Administered concentrated by factor 21)
2) Sample 2 (freeze-dried fermented milk suspended in whey. administered concentrated by factor 5)
3) Sample 3 (freeze-dried fermented milk suspended in neutral pH milk Administered concentrated by factor 5)
4) Sample 4 (just the fermented milk product)
5) Sample 5 (Fermented milk that was heat treated after fermentation)
6) Sample 6 (milk that had not been fermented but it included the live bacteria).

Prior to the experiments all SHR were acclimated to the animal facilities for 9 weeks. More-over, all animals were accustomed to gavage and measurement of systolic blood pressure 3 days before the first gavage.

Investigated Parameters

Systolic blood pressure and heart rate were determined for 24 hours after gavage by telemetry (Data Sciences Int.) in conscious SHR at different time points.

In brief, the mean (over a 1 minute period) of systolic, diastolic blood pressures and heart rate were recorded every 15 minutes, during the 24 hours before administration and the 48 hours after administration.

From these tracings, 24 hours mean of systolic and diastolic blood pressures as well as heart rate were calculated in each group.

Furthermore, the variations in systolic and diastolic blood pressures induced by each substance compared to the untreated values were calculated throughout the 24 hours following gavage, and during the 3 to 6, the 12 to 15 and the 21 to 24 hours periods of time after gavage.

Statistics

All results are expressed as mean±standard error of mean. Differences between the untreated value and the value obtained after gavage of each substance were evaluated using a paired student's t-test, where the calculation was done by using the program SISTAT 8.0.

Results

In table 1 is shown the variation of the heart rate determined.

Table 1:

TABLE 1

| | Heart rate (beats/min) after gavage. | | | | | | | |
|---|---|---|---|---|---|---|---|---|
| | Period | | | | Variation vs. Untreated | | | |
| Group | 0-24 | 3-6 | 12-15 | 21-24 | 0-24 | 3-6 | 12-15 | 21-24 |
| Un- | 320 ± 1 | 291 ± 1 | 343 ± 1 | 319 ± 1 | | | | |
| Sample 1 | 297 ± 2* | 268 ± 2* | 326 ± 8 | 294 ± 3* | −26.4 ± 3.4 | −26.4 ± 5.5 | −19.8 ± 9.3 | −29.7 ± 3.6 |
| Untreated[2] | 330 ± 4 | 291 ± 6 | 361 ± 5 | 289 ± 5 | | | | |
| Sample 2 | 307 ± 6* | 282 ± 6 | 333 ± 11* | 265 ± 4* | −21 ± 3 | −9 ± 5 | −27 ± 8 | −24 ± 4 |
| Sample 3 | 312 ± 6* | 272 ± 8* | 344 ± 5* | 272 ± 5* | −16 ± 1 | −19 ± 5 | −17 ± 4 | −18 ± 4 |
| Sample 4 | 318 ± 6 | 297 ± 6 | 335 ± 6 | 279 ± 7 | −10 ± 3 | 7 ± 6 | −26 ± 4 | −10 ± 6 |
| Sample 5 | 313 ± 5* | 290 ± 6 | 337 ± 6* | 280 ± 5 | −15 ± 4 | −1 ± 7 | −23 ± 5 | −9 ± 4 |
| Sample 6 | 343 ± 9 | 330 ± 17 | 359 ± 9 | 305 ± 5* | 14 ± 9 | 38 ± 17 | −2 ± 7 | 16 ± 7 |

*p < 0.05 vs. Untreated
Untreated[1] and untreated[2] are the controls of study 1 and study number 2, respectively. Untreated1 was the placebo for the sample 1 and untreated 2 was the placebo for all the other samples. We had two placebos because the studies were done independently in two different in vivo studies.

The results demonstrate that the whey product concentrated by a factor 21 (sample 1) has the strongest heart rate reducing properties.

The results demonstrate also that there is no need to up-concentrate the fermented milk product to have already a significant heart rate reducer effect. Samples 4 and 5 are fermented milk products fermented overnight and they have a heart rate reducing effects. However, the heart rate reducer effect is proportional to the concentration factor of the product.

Obviously, the whey part of the product that contains the peptides or other active components is determinant in the heart rate reducer effect. One does observe a dose-heart rate reducing effect of the product.

Sample 3 is freeze-dried fermented milk suspended in neutral pH milk. It reduces the heart rate significantly. This demonstrates the wide application of a fermented product as described herein since it may be dissolved in different liquids to get a required final appropriate use. Characteristic such as different pH are not affecting the heart rate reducer activity of the product.

Sample 5 with heat treatment after fermentation reduces also the heart rate. Substantially all bacteria are killed in this sample. Accordingly, this demonstrates that there is no need to have live bacteria in the final product.

Sample 6 has not been fermented but it includes the live bacteria. It does not reduce the heart rate. It demonstrates that the fermentation step is required.

Example 2

Dose-Response Experiment

To further substantiate the results presented in Example 1, a dose response experiment was performed by administering compositions containing variable amounts of freeze-dried whey obtained from fermented milk suspended in whey from fermented milk to Spontaneously Hypertensive Rats (SHR).

In general, materials and methods and experimental design were as described in Example 1.

In brief, milk was fermented with *Lactobacillus helveticus* strain CHCC5951 (DSM 14998) for 16 hours with an inoculation level of 1% (v/v). The fermented milk was centrifuged, the pellet discarded and the whey freeze-dried. A second fermentation with the same conditions as the first one was centrifuged. The pellet was discarded and the whey was placed at 4° C. The whey was used to solubilize the freeze-dried whey powder resulting in compositions containing solid whey components concentrated 2, 6 and 14.3 times relatively to the amount of solid components in whey obtained in the second fermentation. The final step of the solubilization was done shortly before feeding the composition to the rats.

As in Example 1, unfermented milk was used as placebo.

Starting with the lowest concentration the doses were tested on the same experimental animals in three separate testing-periods. Each testing-period was separated by a "wash out" period of three days in which animals did not received fermented whey product in order to eliminate the activity of the previous dose.

The result is shown in tabular form in table 2.

TABLE 2

| | Heart rate (beats/min) after gavage. | | | | | | | |
|---|---|---|---|---|---|---|---|---|
| | Period | | | | Variation relative to Placebo | | | |
| | 0-24 | 3-6 | 12-15 | 21-24 | 0-24 | 3-6 | 12-15 | 21-24 |
| Untreated | 306 ± 2 | 265 ± 5 | 337 ± 5 | 273 ± 2 | | | | |
| Placebo | 304 ± 2 | 268 ± 2 | 333 ± 3 | 278 ± 4 | −2 | +3 | −4 | +5 |
| Placebo | 314 ± 11 | 282 ± 12 | 335 ± 12 | 295 ± 14 | | | | |
| Concentration 1 | 302 ± 7 | 278 ± 10 | 324 ± 7 | 274 ± 7 | −12 | −4 | −11 | −21 |
| Placebo | 314 ± 9 | 278 ± 8 | 346 ± 9 | 288 ± 8 | | | | |
| Concentration 2 | 309 ± 9 | 287 ± 10 | 334 ± 9 | 289 ± 11 | −5 | +8 | −12 | 1 |
| Placebo | 311 ± 9 | 278 ± 9 | 337 ± 11 | 279 ± 8 | | | | |
| Concentration 3 | 297 ± 9 | 279 ± 15 | 314 ± 7 | 277 ± 10 | −14 | +1 | −24 | −2 |

Note to Table: Untreated rats were not receiving neither milk nor whey product. Placebo is non-fermented milk. Concentration 1, 2 and 3 are whey compositions containing solid whey components concentrated 2, 6 and 14.3 times, respectively. Note that the activity period of the animals is coincident with the period without light, i.e. the time period from 9 to 21.

Figure 1:
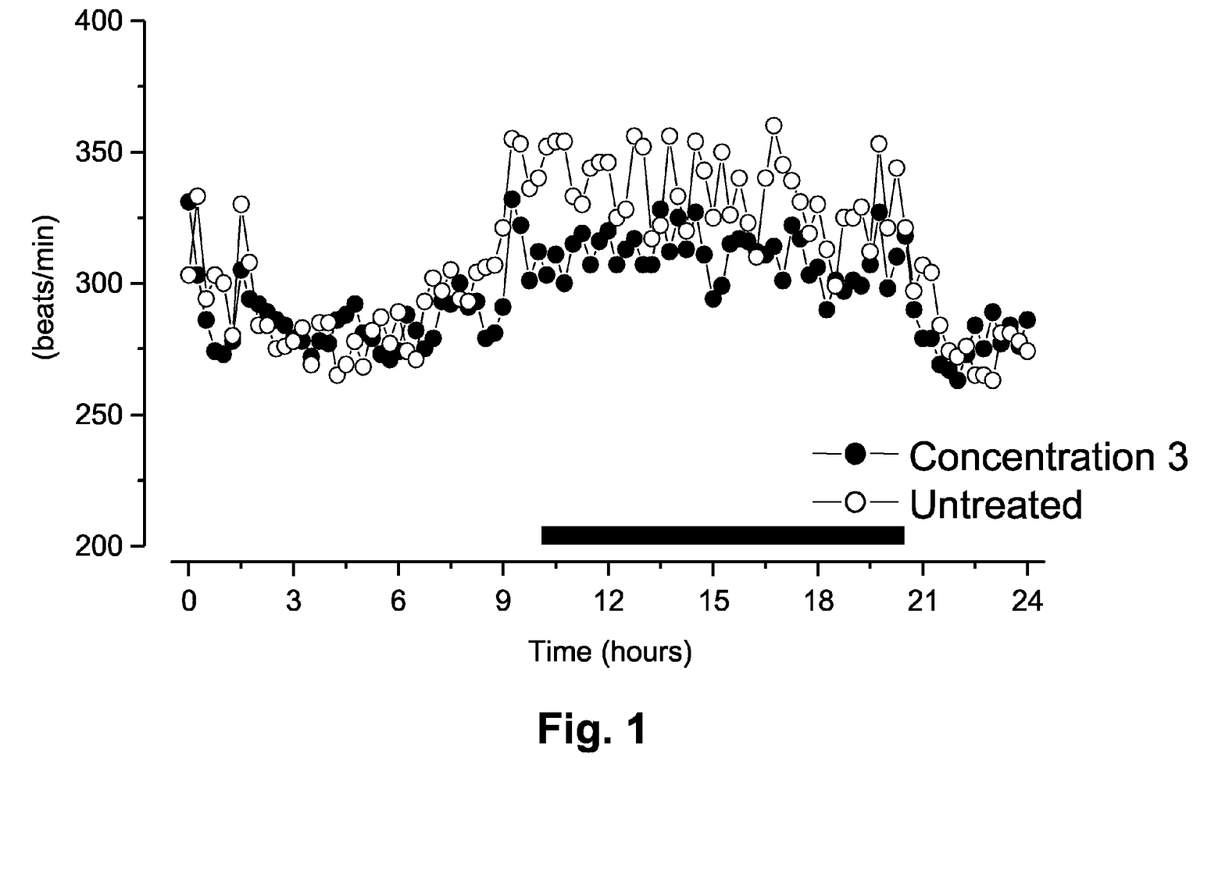
FIG. 1. Heart rate measurements in animals treated with concentration 3 (whey compositions containing solid whey components concentrated factor of 14.3 times) or placebo. Each data point is representing the average value from 8 animals. Note that the activity period of the animals is coincident with the period without light, i.e. the period indicated by the black bar.

In FIG. 1 the results for one full period of concentration 3 (×14.3 concentrated) is shown.

Figure 2:
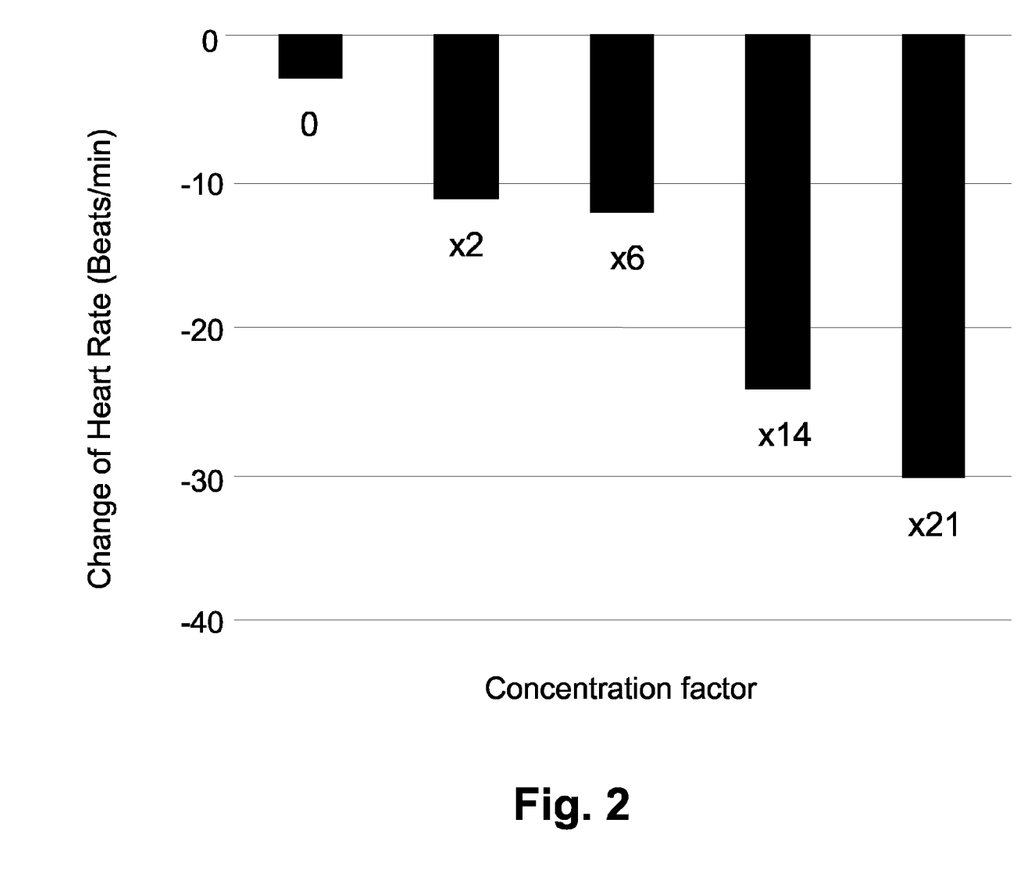
FIG. 2. The reduction in heart rate in animals in the period 12-15 hours after the animals received whey compositions containing solid whey components concentrated 2, 6, 14.3 and 21 times relatively to the amount of solid components in whey obtained after fermentation of milk. The animals were given the whey products by gavage, i.e. feeding by a stomach tube. (O) indicates placebo. The heart rate was determined in animals as described in Example 1 and compared to the heat rate in untreated animals.

In addition freeze-dried whey powder resulting in compositions containing solid whey components concentrated 21 times relatively to the amount of solid components in whey obtained in the second fermentation. The results of feeding animals with a 2, 6, 14.3 as well as a 21 times concentrated whey product are shown in FIG. 2.

The results show a clear dosage dependent effect on the heart rate of the whey products concentrated up to a factor of 21 times. The higher dose of whey products the larger the decrease of heart rate. It appears that a stationary or asymptotic level not was reached, indicating that compositions containing higher concentrations of the active compound(s) can be expected to have higher efficacy for lowering heart rate.

Example 3

Fluctuations in Heart Rate During Period of High Activity is Reduced

During the activity period of the animals the heart rate increase. The activity period of the animals of this investigation is almost coincident with the period without light, i.e. the period indicated by the black bar (see FIG. 1). However, judged from the observations presented in FIG. 1 it appears that not only the heart rate but, surprisingly, also the fluctuations in heart rate is larger in untreated animals compared to animals treated with the 14.3 times concentrated fermented whey product.

To quantify the fluctuations in heart rate the variance of the heart rate values observed in the time period between 12 and 15 h was estimated. The standard deviation was estimated for both treated as well as untreated animals by use of the SISTAT 8.0 program as described in Example 1, and used to calculate the variance ((standard deviation)$^2$=Variance).

The standard deviation for the treated animals was estimated to 5.9, corresponding to a variance of $(5.9)^2=34.8$.

The standard deviation for the untreated animals was estimated to 10.4, corresponding to a variance of $(10.4)^2=108.2$.

Assuming that the primary data are normally distributed a variance of 34.8 is statistically significantly different from a variance of 108.2 at the 95% level.

Thus, it is possible to conclude that the fluctuations in the heart rate during the activity period (measured as variance) are significantly larger in untreated animals compared to the fluctuations in the heart rate of animals treated with the ×14.3 concentrated fermented whey product.

In conclusion, the heart rate fluctuations is stabilized by the whey product fermented with *Lactobacillus helveticus* strain CHCC5951 (DSM 14998). This may be an important feature of the product since it has been observed that changes in heart rate correlated well with mortality in an experimental rabbit model (Zaza et al 2001) and since in particular in stressed situations significant heart rate fluctuations are frequently observed.

Example 4

Comparison of Milk Products Fermented with *L. helveticus* Strain CHCC5951 with a Similar Commercial Product Fermented with a Different Strain The purpose of this example was to compare a commercial lactic acid bacterium fermented milk product that is claimed to have blood pressure reducing properties with the product fermented with *Lactobacillus helveticus* strain CHCC5951 (DSM 14998).

The effect on blood pressure and heart rat of the two products was evaluated by administering the two compositions to Wistar rats and measuring the systolic blood pressure, the diastolic blood pressure and the heart rate on anaesthetized animals.

If not specifically mentioned, materials and methods were as described in Example 1.

In brief, milk was fermented with *Lactobacillus helveticus* strain CHCC5951 (DSM 14998) for 16 hours with an inoculation level of 1% (v/v), and the resulting product was freeze-dried to obtain a freeze dried milk powder. A second fermentation, with the same conditions as the first one, was performed and centrifuged. The pellet was discarded and the whey was filtered through a 0.45 μm filter and frozen. Shortly before feeding it to the rats the freeze-dried milk powder was dissolved in the whey. The amount of powder dissolved corresponded to the amount obtained from a volume of fermented milk that was 5 times the volume of the whey it was dissolved in (in casu 4.28 g powder in 30 ml of whey). This composition we refer to as a ×5 concentration in this example. The composition was administered to overnight fastened normotensive Wistar rats (300-320 grams) between 09:15 h and 09:30 h by gavage at a dose of 7.5 ml per kg of the ×5 composition. The effect of the composition was evaluated between 14:30 h and 16:30 h, i.e. 5-7 hours after the oral administration by measuring the values of arterial blood pressure and heart rate on anaesthetized animals.

The results obtained are shown in table 3.

TABLE 3

Effect of two different fermented products on blood pressure and heart rate.

|  | Untreated | Commercial product | CHCC5951 fermented milk product |
|---|---|---|---|
| Systolic blood pressure (mm Hg) | 134 ± 3 | 125 ± 3* | 125 ± 3* |
| Diastolic blood pressure (mm Hg) | 107 ± 3 | 98 ± 4* | 96 ± 2* |
| Mean blood pressure (mm Hg) | 116 ± 3 | 107 ± 4* | 106 ± 2* |
| Heart Rate (Beats.min-1) | 390 ± 7 | 387 ± 6 | 353 ± 6* |

Values (mean ± SEM) of systolic, diastolic, mean arterial blood pressure and heart rate in the three different groups, 5-7 hours after gavage.
*indicates a significant difference at the p < 0.05 level between treated vs. untreated rats.
The statistical analysis was performed using ANOVA, followed by a Tukey test for multiple comparisons.

From the data it can be concluded that the commercial product and the CHCC5951 fermented product both reduce blood pressure, and furthermore do so to the same extent. However, surprisingly the data in table 3 shows that only the CHCC5951 fermented products significantly reduce the heart rate.

Example 5

The Binding of the Fermented Product to Adrenergic Alpha Receptors

The purpose of this experiment was to investigate which (if any) specific receptors the fermented milk product fermented with *Lactobacillus helveticus* strain CHCC5951 (DSM 14998) could be demonstrated to bind to using in vitro receptor binding assays.

In brief, milk was fermented with *Lactobacillus helveticus* strain CHCC5951 (DSM 14998) for 16 hours with an inoculation level of 1% (v/v). This fermentate was centrifuged, the pellet was discarded and the whey was separated in two parts. One part of the whey was freeze-dried. The other part of the whey was kept at +4° C. until used. This part is referred to as concentration 1×.

The freeze-dried composition was kept at −50° C. until reconstitution in an appropriate diluent. A 200× stock solution was prepared dissolving the freeze dried powder in a volumen of water resulting in a stock solution which was 200× concentrated with respect to whey proteins relative to the non-freeze-dried whey composition.

Competitive in vitro binding assays were prepared on a number of receptors as described in table 4 below:

TABLE 4

Competitive in vitro binding assays

| Family of receptors | receptor assay | biological origin of receptor | compound used for competitition | assay performed as described by |
|---|---|---|---|---|
| Adrenergic | $\alpha_1$ (non-selective) | rat cerebral cortex | prazosin | Greengrass and Bremner (1979) |
| Adrenergic | $\alpha_2$ (non-selective) | rat cerebral cortex | yohimbine | Uhlen and Wikberg (1991) |

The results of the Competitive in vitro binding assays are shown in table 5, below.

TABLE 5

Results of competitive in vitro binding assays

| type of receptor | concentration of fermented product | % Inhibition of Control Specific Binding |
|---|---|---|
| $\alpha_1$ (non-selective) | 0.05 X | 41 |
| $\alpha_1$ (non-selective) | 0, 1 X | 91 |
| $\alpha_1$ (non-selective) | 10 X | 97 |
| $\alpha_1$ (non-selective) | 20 X | 97 |
| $\alpha_2$ (non-selective) | 10 X | 100 |
| $\alpha_2$ (non-selective) | 20 X | 100 |

In the case of the adrenergic $\alpha_1$ receptor the $IC_{50}$ values (concentration causing a half-maximal inhibition of control specific binding) and Hill coefficients ($n_H$) are determined by non-linear regression analysis of the competition curves using Hill equation curve fitting. The inhibition constants ($K_i$) are calculated from the Cheng Prusoff equation ($K_i = IC_{50}/(1+ (L/K_D))$, where L=concentration of radioligand in the assay, and $K_D$=affinity of the radioligand for the receptor). The results were: $IC_{50} = 1.2 \cdot 10^{-9}$ M, Ki=$3.1 \cdot 10^{-10}$ M and $n_H$=0.7.

From the data it can be concluded that food material fermented with *Lactobacillus helveticus* strain CHCC5951 (DSM 14998) comprise components which express a dose-dependent, specific binding to the adrenergic $\alpha_1$ receptor isolated from rat cerebral cortex.

Example 6

The Binding of the Fermented Product to Specific Adrenoreceptors and Muscarinic Receptors The purpose of this experiment was to investigate which specific receptors within the adrenergic and muscarinic receptors, the fermented milk product fermented with *Lactobacillus helveticus* strain CHCC5951 (DSM 14998) could be demonstrated to bind to using in vitro receptor binding assays.

Materials and Methods

In brief, milk which was fermented with *Lactobacillus helveticus* strain CHCC5951 (DSM 14998) for 16 hours with an inoculation level of 1% (v/v). This fermentate was centrifuged, the pellet was discarded and the whey was kept at +4° C. until used. This part is referred to as concentration 1x.

The receptor-binding assays were performed essentially as described in table 6 as described in the literature indicated in table 7. The results of the receptor-binding assays are presented in table 8.

TABLE 6

Receptor-binding assays.

| Assay | Ligand | Conc. | Non Specific | Incubation | Method of Detection |
|---|---|---|---|---|---|
| $\alpha_{1A}$(h) | [$^3$H] prazosin | 0.06 nM | prazosin (10 μM) | 60 min./ 22° C. | Scintillation counting |
| $\alpha_{1B}$(h) | [$^3$H] prazosin | 0.05 nM | prazosin (10 μM) | 60 min./ 22° C. | Scintillation counting |
| $\alpha_2$ A(h) | [$^3$H]RX 821002 | 1 nM | (-) epinephrine (100 μM) | 30 min./ 22° C. | Scintillation counting |
| $\alpha_2$ B(h) | [$^3$H]RX 821002 | 2.5 nM | (-) epinephrine (100 μM) | 30 min./ 22° C. | Scintillation counting |
| $\beta_1$ (h) | [$^3$H](-)CPG 12177 | 0.15 nM | alprenolol (50 μM) | 60 min./ 22° C. | Scintillation counting |
| $\beta_2$ (h) | [$^3$H](-)CGP 12177 | 0.15 nM | alprenolol (50 μM) | 60 min./ 22° C. | Scintillation counting |
| $\beta_3$ (h) | [$^{125}$I]CYP (+ 1 μM (-) propranol) | 0.6 nM | (-) propranolol (1 mM) | 90 min./ 37° C | Scintillation counting |
| 5-HT (non-selective | [$^3$H] serotonin | 2 nM | serotonin (10 μM) | 15 min./ 37° C. | Scintillation counting |

TABLE 7

Competitive in vitro binding assays

| Family of receptors | receptor assay | biological origin of receptor | compound used for competitition | assay performed as described by |
|---|---|---|---|---|
| Adrenergic | $\alpha_1$A | rat salivary glands | WB4101 | Michel et al. (1989) |
| Adrenergic | $\alpha_{1B}$ | rat liver | spiperone | Michel et al. (1989) |

TABLE 7-continued

Competitive in vitro binding assays

| Family of receptors | receptor assay | biological origin of receptor | compound used for competitition | assay performed as described by |
|---|---|---|---|---|
| Adrenergic | $\alpha_{2A}$(h) | human recombinant (CHO cells) | yohimbine | Langin et al. (1989) |
| Adrenergic | $\alpha_{2B}$(h) | human recombinant (CHO cells) | yohimbine | Devedjian et al. (1994) |
| Adrenergic | $\alpha_{2C}$(h) | human recombinant (CHO cells) | yohimbine | Devedjian et al. (1994) |
| Adrenergic | $\beta_{1(h)}$ | human recombinant (HEK-293 cells) | atenolol | Levin et al. (2002) |
| Adrenergic | $\beta_{2(h)}$ | human recombinant (Sf9 cells) | ICI 118551 | Smith and Teitler (1999) |
| Adrenergic | $\beta_{3(h)}$ | SK-N-MC cells recombinant (Sf9 cells) | cyan-opindolol | Curran and Fishman (1996) |
| Serotonin | 5-HT (non-selective) | rat cerebral cortex | serotonin | Peroutka and Snyder (1979) |

TABLE 8

Results of competitive in vitro binding assays

| type of receptor | concentration of fermented product | % Inhibition of Control Specific Binding |
|---|---|---|
| $\alpha_1$A | 0.05 X | −11 |
| | 0.1 X | 78 |
| $\alpha_{1B}$ | 0.05 X | 18 |
| | 0.1 X | 76 |
| $\alpha_{2A}$(h) | 0.05 X | 37 |
| | 0.1 X | 91 |
| $\alpha_{2B}$(h) | 0.05 X | 43 |
| | 0.1 X | 93 |
| $\alpha_{2C}$(h) | 0.05 X | 13 |
| | 0.1 X | 86 |
| $\beta_{1(h)}$ | 0.05 X | 16 |
| | 0.1 X | 62 |
| $\beta_{2(h)}$ | 0.05 X | 83 |
| | 0.1 X | 103 |
| $\beta_{3(h)}$ | 0.05 X | −2 |
| | 0.1 X | 28 |
| 5-HT (non-selective) | 0.05 X | 65 |
| | 0.1 X | 120 |

From the data it can be concluded that food material fermented with *Lactobacillus helveticus* strain CHCC5951 (DSM 14998) comprise components which express a dose-dependent, specific binding to the adrenoreceptors and serotonin receptors.

More than one receptor is inhibited, underlining the complexity of the composition of the supernatant. The various effects are most likely effected by different peptides with different target profiles.

In conclusion, the compounds present in the whey of the fermentate expresses the highest hibitory activity on the beta 2(h) (average 93%) and 5-HTns (average 93%) receptors, followed by alpha 2B(h)(average 68%)>alpha 2A(h) (average 64%)>alpha 2C(h) (average 50%) and alpha 1B(h) (average 47%). At a lower level, the compounds inhibit the receptors beta 1(h) (average 39%) and alpha 1A(h) (average 34%).

The compounds are not active on the receptor beta3(h).

REFERENCES

EP821968 (Calpis Food Industry)
EP1016709 (Calpis Food Industry)
WO0132836 (Valio Ltd.).
WO0185984 (Davisco International Foods, Inc.)
Altwein (1995) The changing therapy of benign prostatic hyperplasia. Scand J Urol Nephrol Suppl.; 168:1-6
Barry and Roehrborn (1997), Management of benign prostatic hyperplasia. Annu Rev Med, 48:177-89).
Brindley G S (1986) Pilot experiments on the actions of drugs injected into the human corpus cavernosum penis. Br J Pharmacol 87: 495-500.
Curran, P. K. and Fishman, P. H. (1996) Endogenous $\beta_3$- but not $\beta_1$-adrenergic receptors are resistant to agonist-mediated regulation in human SK-N-MC neurotumor cells. Cell Signal, 8: 355-364.
Devedjan, J. C., Esclapez, F., Denis-Ploxviel, C., and Paris, H., (1994) Further characterization of human $\alpha_2$-adrenoreceptor subtypes: [$^3$H]RX82102 binding and definition of additional selective drugs. Eur. J. Pharmacol., 252: 43-49.
Fuglsang, A.; et al. (2002) Applied and Environmental Microbiology, 3566-3569.
Fuller R. (1989) Probiotics in man and animals. J Appl Bacteriol 66: 365-78.
Greengrass, P. and Bremner, R. (1979) Binding characteristics of [$^3$H]-prazosin to rat brain alpha-adrenergic receptors. Eur. J. Pharmacol., 55: 323-326.
Kenny, B. et al. (1995) Alpha 1-Adrenoreceptor Antagonists As Treatments For Benign Prostatic Hyperplasia, Exp. Opin. Invest. Drugs, (1995), 4 (10), 915-23
Kim N N et al. (2000) Alpha-adrenergic receptor blockade by phentolamine increases the efficacy of vasodilators in penile corpus cavernosum. Int J Impot Res. 12 Suppl 1:S26-36.
Langin, D., Lafontan, M., Stilling, M. R., and Paris, H. (1989) [$^3$H]RX82102: a new tool for the identification of $\alpha_2$-adrenoreceptors. Eur. J. Pharmacol., 167: 95-104.
Levin, M. C., Marullo, S., Muntaner, O., Anderson, B. and Magnusson, Y. (2002). The myocardium-protective Gly-49 variant of the beta 1-adrenergic receptor exhibits constitutive activity and increased desensitization and down regulation. J. Biol. Chem. 277: 30429-30435
Michel, A. D., Loury, D. N. and Whiting, R. L. (1989) Identification of a single $\alpha_1$-adrenoreceptor corresponding to the $\alpha_{1A}$-subtype in rat submaxillary gland. Brit. J. Pharmacol., 98: 883-889.
Morales (2000) Yohimbine in erectile dysfunction: the facts. Int J Impot Res. 12 (Suppl 1): S70-S74.
Peroutka, S. J. and Snyder, S. H. (1979) Multiple serotonin receptors: differential binding of [$^3$H]5-hydroxytryptamine, [$^3$H]lysergic acid diethylamide and [$^3$H] spiroperidol. Mol. Pharmacol., 16: 687-699.
Ronald F. Borne (1994) Serotonin: The Neurotransmitter for the '90s. Drug Topics, Oct. 10, 1994, p. 108 (http://web.tampabay.rr.com/lymecfs/seroton.htm).
Smith, C. and Teitler, M. (1999) Beta-blocker selectivity at cloned human beta$_1$- and beta$_2$-adrenergic receptors. Cardiovasc. Drugs Ther., 13: 123-126.
Uhlen, S. and Wikberg, J. E. (1991) Rat spinal chord $\alpha$2-adrenoceptors are of the $\alpha$2A-subtype: comparison with $\alpha$2A- and $\alpha$2B-adrenoceptors in rat spleen, cerebral cortex and kidney using $^3$H-RX821002 ligand binding. Pharmacol. Toxicol., 69: 341-350.
Yamamoto et al. (1996) Am. J. Clin. Nurt., 64:767-71.
Zaza, A., T. Opthof, J. Camm, F. Lombardi and S. Hohnloser (2001) "Heart rate reduction: optimism with some caveats". nEwSCast Report presented to the XXIII'th Congress of the European Society of Cardiology, Stockholm 2001 (http://ftp.escardio.org/newscast/archivesstock.htm).

Regarding Deposited Microbial Organisms [Expert Solution]

For all deposited microbial organisms mentioned in the present patent application the following applies.

Europe

In respect to those designations in which a European Patent is sought a sample of the deposited microorganism will be made available until the publication of the mention of the grant of the European patent or until the date on which application has been refused or withdrawn or is deemed to be withdrawn, only by the issue of such a sample to an expert nominated by the person requesting the sample, and approved either i) by the Applicant and/or ii) by the European Patent Office, whichever applies. (Rule 28 (4) and 28 (5) EPC).

Canada

The applicant requests that, until either a Canadian patent has been issued on the basis of an application or the application has been refused, or is abandoned and no longer subject to reinstatement, or is withdrawn, the Commissioner of Patents only authorizes the furnishing of a sample of the deposited biological material referred to in the application to an independent expert nominated by the Commissioner, the applicant must, by a written statement, inform the International Bureau accordingly before completion of technical preparations for publication of the international application.

Norway

The applicant hereby requests that, until the application has been laid open to public inspection (by the Norwegian Patent Office), or has been finally decided upon by the Norwegian Patent Office without having been laid open inspection, the furnishing of a sample shall only be effected to an expert in the art. The request to this effect shall be filed by the applicant with the Norwegian Patent Office not later than at the time when the application is made available to the public under Sections 22 and 33 (3) of the Norwegian Patents Act. If such a request has been filed by the applicant, any request made by a third party for the furnishing of a sample shall indicate the 'expert to be used. That expert may be any person entered on the list of recognized experts drawn up by the Norwegian Patent Office or any person approved by the applicant in the individual case.

Australia

The applicant hereby gives notice that the furnishing of a sample of a microorganism shall only be effected prior to the grant of a patent, or prior to the lapsing, refusal or withdrawal of the application, to a person who is a skilled addressee without an interest in the invention (Regulation 3.25(3) of the Australian Patents Regulations).

Finland

The applicant hereby requests that, until the application has been laid open to public inspection (by the National Board of Patents and Regulations), or has been finally decided upon by the National Board of Patents and Registration without having been laid open to public inspection, the furnishing of a sample shall only be effected to an expert in the art.

United Kingdom

The applicant hereby requests that the furnishing of a sample of a microorganism shall only be made available to an expert. The request to this effect must be filed by the applicant with the International Bureau before the completion of the technical preparations for the international publication of the application.

Denmark

The applicant hereby requests that, until the application has been laid open to public inspection (by the Danish Patent Office), or has been finally decided upon by the Danish Patent office without having been laid open to public inspection, the furnishing of a sample shall only be effected to an expert in the art. The request to this effect shall be filed by the applicant with the Danish Patent Office not later that at the time when the application is made available to the public under Sections 22 and 33(3) of the Danish Patents Act. If such a request has been filed by the applicant, any request made by a third party for the furnishing of a sample shall indicate the expert to be used. That expert may be any person entered on a list of recognized experts drawn up by the Danish Patent Office or any person by the applicant in the individual case.

Sweden

The applicant hereby requests that, until the application has been laid open to public inspection (by the Swedish Patent Office), or has been finally decided upon by the "Swedish Patent Office without having been laid open to public inspection, the furnishing of a sample shall only be effected to an expert in the art. The request to this effect shall be filed by the applicant with the International Bureau before the expiration of 16 months from the priority date (preferably on the Form PCT/RO/134 reproduced in annex Z of Volume I of the PCT Applicant's Guide). If such a request has been filed by the applicant any request made by a third party for the furnishing of a sample shall indicate the expert to be used. That expert may be any person entered on a list of recognized experts drawn up by the Swedish Patent Office or any person approved by a applicant in the individual case.

Netherlands

The applicant hereby requests that until the date of a grant of a Netherlands patent or until the date on which the application is refused or withdrawn or lapsed, the microorganism shall be made available as provided in the 3 IF(1) of the Patent Rules only by the issue of a sample to an expert. The request to this effect must be furnished by the applicant with the Netherlands Industrial Property Office before the date on which the application is made available to the public under Section 22C or Section 25 of the Patents Act of the Kingdom of the Netherlands, whichever of the two dates occurs earlier.

The invention claimed is:

1. A method of treating or preventing benign prostate hypertrophy (BPH) and/or erectile dysfunction in a mammal, comprising administering to said mammal a composition that (A) comprises a ligand of an adrenergic or a serotonin receptor and (B) is prepared by fermenting, with at least one lactic acid bacterial strain, a food material comprised of animal milk or vegetable proteins, wherein said strain is a *Lactobacillus helveticus* strain represented by accession number DSM 14998.

2. The method according to claim 1, wherein said receptor is selected from the group of receptors comprising alpha-adrenergic receptors, beta-adrenergic receptors and serotonin receptors.

3. The method according to claim 2, wherein said receptor is selected from the group of receptors comprising the $alpha_1A$-, the $alpha_1B$-, the $alpha_{2A}(h)$-, the $alpha_{2B}(h)$-, the $alpha_{2C}(h)$-, the $beta_1(h)$-, the $beta_2(h)$- and the $beta_3(h)$-adrenergic receptor and serotonin receptors.

4. The method according to claim 3, wherein said receptor is selected from the group of receptors comprising the $alpha_{2A}(h)$-, the $apha_{2B}(h)$- and the $beta_2(h)$-adrenergic receptor.

5. The method according to claim 1, wherein said ligand of said receptor has the characteristics of being an antagonist of the receptor.

6. The method according to claim 1, wherein the composition is a food or feed product.

7. The method according to claim 1, wherein said administration reduces the heart rate of said mammal.

8. The method according to claim 1, wherein said composition further comprises at least one ligand of the GABA receptor.

9. The method according to claim 8, wherein said ligand to the GABA receptor is GABA produced by GABA-producing microorganisms included amongst microorganisms used to perform said fermentation.

10. The method according to claim 1, further comprising at least one component selected from the group consisting of nitric oxide and an inhibitor of phosphodiesterase-5 or 5-alpha reductase.

11. The method according to claim 1, wherein the composition is fermented using a combination of at least two lactic acid bacteria.

12. The method according to claim 11, wherein the composition is fermented using *Lactobacillus helveticus* strain DSM 14998 and a lactic acid bacterium of *Streptococcus thermophilus*.

* * * * *